(12) United States Patent
Takesue et al.

(10) Patent No.: US 9,056,884 B2
(45) Date of Patent: Jun. 16, 2015

(54) PROCESS FOR PRODUCING A CHARGE CONTROL AGENT

(71) Applicant: HODOGAYA CHEMICAL CO., LTD., Tokyo (JP)

(72) Inventors: Atsushi Takesue, Tokyo (JP); Yoshihiko Abe, Tokyo (JP); Hideyuki Otsuka, Tokyo (JP); Jun Watanabe, Tokyo (JP); Shunsuke Saitoh, Tokyo (JP); Kanae Hiraishi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 13/785,395

(22) Filed: Mar. 5, 2013

(65) Prior Publication Data

US 2014/0171628 A1    Jun. 19, 2014

Related U.S. Application Data

(60) Provisional application No. 61/736,736, filed on Dec. 13, 2012.

(51) Int. Cl.
    C09B 45/01    (2006.01)
    C07F 15/02    (2006.01)
    C07C 245/10   (2006.01)

(52) U.S. Cl.
    CPC ............... *C07F 15/025* (2013.01); *C09B 45/01* (2013.01); *C07C 245/10* (2013.01)

(58) Field of Classification Search
    CPC .................................................... C09B 45/01
    USPC ..................................... 430/108.23; 534/602
    See application file for complete search history.

(56) References Cited

U.S. PATENT DOCUMENTS 7,094,513 B2 *    8/2006    Yasumatsu et al. ....... 430/108.23

FOREIGN PATENT DOCUMENTS

| JP | 58-111049 | 7/1983 |
| JP | 61-101558 | 5/1986 |
| JP | 61-155464 | 7/1986 |

OTHER PUBLICATIONS

U.S. Appl. No. 61/736,736 to Atsushi Takesue et al., filed Dec. 13, 2012.

* cited by examiner

*Primary Examiner* — Robert Havlin
(74) *Attorney, Agent, or Firm* — Greenblum & Bernstein, P.L.C.

(57) ABSTRACT

A process for producing a charge control agent comprising an azo-based iron complex salt compound as an effective component, comprises:
  synthesizing a monoazo compound through diazotization coupling; and
  ironing the monoazo compound by using an ironizing agent such as ferric chloride to produce an azo-based iron complex salt compound represented by the following formula.

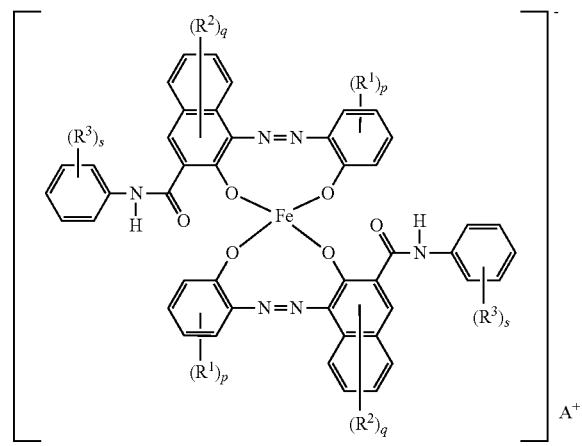

The ironization reaction of the monoazo compound is carried out while pH is kept at 7.0 to 8.0. Since the above azo-based iron complex salt compound having high purity can be obtained at a high yield, it can be used as a charge control agent directly and a special purification step can be eliminated, thereby making it possible to greatly cut the production cost.

3 Claims, 1 Drawing Sheet

PROCESS FOR PRODUCING A CHARGE CONTROL AGENT

CROSS-REFERENCE TO RELATED APPLICATIONS

This application claims the benefit of U.S. Provisional Application No. 61/736,736, filed Dec. 13, 2012.

BACKGROUND OF THE INVENTION

1. Field of the Invention

The present invention relates to a process for producing a charge control agent which comprises an azo-based iron complex salt having negative chargeability and high environmental safety.

2. Prior Art

In an image forming process of electrophotographic system employed in copiers and printers, the surface of a photoreceptor is charged (main charging), an electrostatic latent image corresponding to a target image is formed by exposure to light (image exposure), this electrostatic image is visualized by a charged toner (development), the formed toner image is transferred onto paper or plastic film (transfer), and the transferred toner image is fixed by heat or pressure (fixing) to obtain a target visible image.

In the above image forming process, an inorganic photoreceptor such as selenium, selenium alloy, cadmium sulfide or amorphous silicon, or an organic photoreceptor containing a charge generating agent and a charge transport agent is used as the photoreceptor.

Powders containing a colorant and another additive dispersed in a binder resin are used as a toner for development.

A typical example of the above additive contained in the toner is a charge control agent which is used to secure desired charging characteristics (such as charging risetime, charging level and charging stability).

Negatively chargeable azo-based metal complex salts (for example, azo-based complex salts such as iron, cobalt and chromium complex salts) are proposed as the charge control agent in Patent Documents 1 to 3.

When the above azo-based metal complex salts are used, the charging risetime of the toner can be accelerated, the toner can be fully negatively charged quickly, the amount of charge can be stabilized while it is suitably controlled, and a clear image can be formed while the development speed of an electrostatic latent image is accelerated. Out of these azo-based metal complex salts, an iron complex salt has high environmental safety and is of extremely great industrial value.

The charge control agent is also used in a powdery coating material which is used for electrostatic coating, charges in predetermined polarity, is coated on the surface of a target structure such as a car body by making use of electrostatic attractive force and can form a coating film on the surface of the structure by baking it. The excellent charging ability of the above-described negatively chargeable azo-based charge control agent is exhibited even for this powdery coating material.

PRIOR ART DOCUMENTS

Patent Documents

[Patent Document 1] JP-A 61-155464
[Patent Document 2] JP-A 61-101558
[Patent Document 3] JP-A 58-111049

SUMMARY OF THE INVENTION

Problem to be Solved by the Invention

An object of the present invention is to provide a process capable of producing a charge control agent comprising an azo-based iron complex salt having excellent charging ability and high environmental safety at low cost.

Means for Solving the Problem

According to the present invention, there is provided a process for producing a charge control agent comprising an azo-based iron complex salt compound as an effective component, comprising steps of:

(A) obtaining a monoazo compound represented by the following general formula (1) through diazotization coupling;

(1)

wherein,
p is an integer of 0 to 4 indicative of the number of $R^1$ group,
q and s are each an integer of 0 to 5 indicative of the numbers of $R^2$ group and $R^3$ group, respectively, and
$R^1$ to $R^3$ are each a deuterium atom, halogen atom, nitro group, hydroxyl group, alkyl group, alkenyl group, alkyloxy group, sulfonalkyl group, alkylsulfonate group, sulfonate group, carboxyl group, carboxyester group, sulfonamide group, acetylamino group, benzoylamino group, aromatic hydrocarbon group or aromatic heterocyclic group, with the proviso that when a plurality of $R^1$ groups, $R^2$ groups or $R^3$ groups are existent, said $R^1$ groups, said $R^2$ groups or said $R^3$ groups may be different from one another); and (B) ironizing the monoazo compound in a solvent while pH is kept at 7.0 to 8.0 to produce an azo-based iron complex salt compound represented by the following general formula (2);

(2)

wherein, p, q, s and $R^1$ to $R^3$ are as defined in the above general formula (1), and $A^+$ is a cation.

In the present invention, preferably, the above process further comprises a step (C) of introducing an ammonium ion as cationic species into the charge control agent through ion exchange.

Effect of the Invention

According to the production process of the present invention, since the above azo-based iron complex salt compound having high purity can be obtained at a high yield, it can be used as a charge control agent directly and a special purification step can be eliminated, thereby making it possible to greatly cut its production cost.

The charge control agent of the present invention which is obtained as described above has excellent environmental safety, can provide excellent negatively charging characteristics, can accelerate the charging risetime of a toner and can secure a sufficiently large amount of charge quickly when it is mixed with the toner, has excellent stability of charge amount and makes it possible to form a clear high-resolution image.

As a matter of course, this charge control agent can be used not only as an additive for toners but also as an additive for powder coating materials.

BEST MODE FOR CARRYING OUT THE INVENTION

The process for producing a charge control agent according to the present invention comprises (A) a coupling step for obtaining a monoazo compound through a diazotization coupling reaction and (B) an iron complex salt forming step for ironizing the monoazo compound and further, preferably, (C) an ion exchange step for introducing specific cationic species. After these steps, the obtained product is granulated by an ordinary post-step to be used as a charge control agent.

A description is subsequently given of each of the above steps.

(A) Coupling Step:

In this coupling step, a monoazo compound represented by the following general formula (1) is synthesized.

(1)

In the above general formula (1), p is an integer of 0 to 4 indicative of the number of group $R^1$'s, and q and s are each an integer of 0 to 5 indicative of the numbers of group $R^2$'s and group $R^3$'s, respectively.

In the above general formula (1), $R^1$ to $R^3$ are each a deuterium atom, halogen atom, nitro group, hydroxyl group, alkyl group, alkenyl group, alkyloxy group, sulfonalkyl group, alkylsulfonate group, sulfonate group, carboxyl group, carboxylester group, sulfonamide group, acetylamino group, benzoylamino group, aromatic hydrocarbon group or aromatic heterocyclic group and may be the same or different.

Further, when a plurality of $R^1$'s, $R^2$'s or $R^3$'s are existent, that is, p, q or s is an integer of 2 or more, $R^1$'s, $R^2$'s or $R^3$'s may be different from one another.

In the above $R^1$ to $R^3$, examples of the halogen atom are fluorine atom, chlorine atom, bromine atom and iodine atom.

The alkyl group may be linear or branched and the number of carbon atoms thereof is preferably 1 to 18. Examples thereof include methyl group, ethyl group, n-propyl group, isopropyl group, n-butyl group, isobutyl group, tert-butyl group, n-pentyl group, isopentyl group, neopentyl group, n-hexyl group, n-heptyl group, isoheptyl group, n-octyl group, isooctyl group, n-nonyl group, n-decyl group, n-dodecyl group, n-hexadecyl group and n-octadecyl group.

The alkyloxy "(sic)" group may also be linear or branched and the number of carbon atoms thereof is preferably 2 to 18. Examples thereof include vinyl group, allyl group, isopropenyl group, 2-butenyl group, n-hexenyl group, n-heptenyl group, isoheptenyl group, n-octenyl group, isooctenyl group, n-nonenyl group, n-decenyl group, n-dodecenyl group, n-hexadecenyl group and n-octadecenyl group.

The above alkyloxy group may also be linear or branched and the number of carbon atoms thereof is preferably 1 to 18. Examples thereof include methyloxy group, ethyloxy group, n-propyloxy group, isopropyloxy group, n-butyloxy group, tert-butyloxy group, n-pentyloxy group, n-hexyloxy group, n-heptyloxy group, isoheptyloxy group, n-octyloxy group, isooctyloxy group, n-nonyloxy group, n-decyloxy group, n-dodecyloxy group, n-hexadecyloxy group and n-octadecyloxy group.

The sulfonalkyl group has a sulfonate group bonded to an alkyl group as a substituent. The alkyl group has 1 to 6 carbon atoms, as exemplified by methyl group, ethyl group, n-propyl group, isopropyl group, n-butyl group, isobutyl group, tert-butyl group, n-pentyl group, isopentyl group, neopentyl group, n-hexyl group, n-heptyl group, isoheptyl group, n-octyl group and isooctyl group.

The alkylsulfonate group has an alkyl group bonded to a sulfonate group as a substituent. This alkyl group preferably has 1 to 6 carbon atoms, as exemplified by the same alkyl groups as those enumerated for the sulfonalkyl group.

The aromatic hydrocarbon group and the aromatic heterocyclic group may have a monocyclic structure or a condensation polycyclic structure.

Examples of the aromatic hydrocarbon group include phenyl group, biphenylyl group, terphenylyl group, naphthyl group, anthracenyl group, phenanthryl group, fluorenyl group, indenyl group, pyrenyl group, perylenyl group, fluoranthenyl group and triphenylenyl group.

Examples of the aromatic heterocyclic group include pyridyl group, furanyl group, pyranyl group, thienyl group, furyl group, pyrrolyl group, pyrrolidinyl group, imidazolyl group, imidazolinyl group, imidazolidinyl group, pyrazolyl group, pyrazolinyl group, pyrazolidinyl group, pyridazinyl group, pyrazinyl group, piperidinyl group, piperazinyl group, thiolanyl group, thianyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group and carbolinyl group.

The groups represented by the above $R^1$ to $R^3$ may each have a substituent. Under the condition that substituents having a limited number of carbon atoms should have the limited number of carbon atoms, examples of the substituents include deuterium atom; trifluoromethyl group; cyano group; nitro group; hydroxyl group; halogen atoms such as fluorine atom, chlorine atom, bromine atom and iodine atom; alkyl groups having 1 to 8 carbon atoms such as methyl group, ethyl group, n-propyl group, isopropyl group, n-butyl group, isobutyl group, tert-butyl group, n-pentyl group, isopentyl group, neopentyl group, n-hexyl group, n-heptyl group, isoheptyl group, n-octyl group and isooctyl group; alkyloxy groups having 1 to 8 carbon atoms such as methyloxy group, ethyloxy group and propyloxy group; alkenyl groups such as allyl group; aralkyl groups such as benzyl group, naphthylmethyl group and phenethyl group; aryloxy groups such as phenyloxy group and tolyloxy group; arylalkyloxy groups such as benzyloxy group and phenethyloxy group; aromatic hydrocarbon groups such as phenyl group, biphenylyl group, terphenylyl group, naphthyl group, anthracenyl group, phenanthryl group, fluorenyl group, indenyl group, pyrenyl group, perylenyl group, fluoranthenyl group and triphenylenyl group; heterocyclic groups such as pyridyl group, furanyl group, pyranyl group, thienyl group, furyl group, pyrrolyl group, pyrrolidinyl group, imidazolyl group, imidazolinyl group, imidazolidinyl group, pyrazolyl group, pyrazolinyl group, pyrazolidinyl group, pyridazinyl group, pyrazinyl group, piperidinyl group, piperazinyl group, thiolanyl group, thianyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group and carbolinyl group; arylvinyl groups such as styryl group and naphthylvinyl group; acyl groups such as acetyl group and benzoyl group; dialkylamino groups such as dimethylamino group and diethylamino group; di-substituted amino groups substituted by an aromatic hydrocarbon group or condensation polycyclic aromatic group such as diphenylamino group and dinaphthylamino group; diaralkylamino groups such as dibenzylamino group and diphenethylamino group; di-substituted amino groups substituted by a heterocyclic group such as dipyridylamino group, dithienylamino group and dipiperidinylamino group; dialkenylamino groups such as diallylamino group; and di-substituted amino groups having a substituent selected from alkyl group, aromatic hydrocarbon group, aralkyl group, heterocyclic group and alkenyl group.

These substituents may further have a substituent.

The coupling step for synthesizing the above monoazo compound is known and may be carried out, for example, by the method of the above Patent Document 3.

Stated more specifically, to produce the monoazo compound of the general formula (1) through diazotization coupling, an aminophenol derivative corresponding to the structure of the monoazo compound is used as a starting material and diazotized to prepare a diazonium salt, and a naphthol derivative (for example, Naphthol AS) corresponding to the structure of the monoazo compound is coupled to the diazonium salt.

The above diazotization is carried out by causing sodium nitrite to act on the aminophenol derivative in an acidic aqueous solution such as a hydrochloric acid aqueous solution, thereby making it possible to obtain a diazonium salt of the aminophenol derivative.

Since this diazotization reaction is an exothermic reaction, it is preferred to carry out the reaction while the reaction temperature is kept at 5 to 15° C., particularly 5 to 10° C. by cooling with ice.

Coupling which is carried out after diazotization is carried out preferably in a mixed solution of water and an organic solvent, more preferably in a mixed solution of water and a lower alcohol having 1 to 6 carbon atoms, particularly preferably in a mixed solution of water and n-butanol and most preferably under a basic condition.

For example, it is most advantageous that the coupling reaction should be carried out by adding the above naphthol derivative and an alkali aqueous solution such as a sodium hydroxide aqueous solution to the above mixed solution containing the diazonium salt synthesized by diazotization and keeping pH at 11 to 12 and the temperature at 15 to 25° C. (particularly 20 to 24° C.).

The above diazotization and coupling may be carried out in the same reactor, or the reaction solution containing an intermediate product (diazonium salt) may be taken out from the reactor after the end of diazotization and transferred to another reactor.

The reaction product (monoazo compound of the general formula (1)) obtained by the above coupling may be supplied to the subsequent step (iron complex salt forming step) directly or after it is filtered with a Nutsche filter or a filter press or after it is taken out as a wet cake by centrifugal filtration and suitably dried as required.

(B) Iron Complex Salt Forming Step:

The monoazo compound obtained by the above step is subjected to an ironizing reaction to produce an azo-based iron complex salt compound represented by the following general formula (2) which has a structure that two molecules of the monoazo compound are coordinated to an iron atom.

(2)

In the above general formula (2), p, q, s and $R^1$ to $R^3$ are as defined in the above general formula (1), and $A^+$ is a cation.

This ironizing reaction is carried out by dissolving or dispersing the reaction product containing the monoazo compound obtained above in a solvent, heating this reaction solution, and adding an aqueous solution of an ironizing agent dropwise to this reaction solution to react the monoazo compound with the ironizing agent. Although the ironizing agent is not limited to this, ferric chloride, ferric sulfate, ferrous sulfate and ferric nitrate are generally used as the ironizing agent, out of which ferric chloride is advantageously used from the viewpoints of material cost, handling ease and reactivity.

The amount of the ironizing agent is ½ to 2 equivalents, preferably ½ to ⅔ equivalents in terms of the metal atom based on 1 equivalent of the monoazo compound as a ligand.

When the ironizing reaction is promoted by adding an aqueous solution of the ironizing agent, pH of the reaction solution becomes acidic. However, it is important in the present invention that pH of the reaction solution should be kept at 7.0 to 8.0, particularly 7.0 to 7.5. That is, the ironizing reaction is carried out by adding a basic compound to this reaction solution so as to adjust pH to the above range.

Fine crystal particles of the azo-based iron complex salt compound of the above general formula (2) can be obtained by carrying out this pH control. For example, the primary particle diameter of the azo-based iron complex salt compound becomes small, the yield and purity of the compound become extremely high, the particle diameter of an agglomerate of the compound becomes small, and pulverization can be easily carried out. That is, when pH is outside the above range, the primary particle diameter of the formed azo-based iron complex salt becomes large with the result that the yield and purity of the compound degrade, the particle diameter of the agglomerate becomes large, a burden for pulverizing the compound to such a small particle diameter that it can be uniformly dispersed in a binder resin as a charge control agent becomes large, and the object of the present invention which is to reduce the production cost cannot be attained.

As the basic compound used to control pH in the present invention, a hydroxide or carbonate of an alkali metal is used, sodium hydroxide or potassium hydroxide is particularly preferably used, and sodium hydroxide is most preferably used from the viewpoints of material cost and handling ease.

That is, the ironizing reaction while pH is controlled is carried out by adding an aqueous solution containing the above basic compound and the ironizing agent dropwise.

In the above ironizing reaction, the reaction temperature is preferably 60±10° C., more preferably 60±5° C., and the reaction time may be short at 7 to 8 hours.

Further, as the solvent used in the above reaction, that is, the solvent for dissolving or dispersing the reaction product containing the monoazo compound, a mixed solvent of water and an organic solvent is advantageously used.

Examples of the organic solvent used in combination with water include hydrophilic organic solvents, amide-based solvents, ether-based solvents, ketone-based solvents, sulfoxide-based solvents and aromatic hydrocarbon-based solvents, out of which hydrophilic solvents are preferred.

The hydrophilic organic solvents include alcohols such as ethanol, n-propanol, isopropanol, n-butanol, amyl alcohol, benzyl alcohol, cyclohexanol and diacetone alcohol; monoalkyl ethers of a glycol such as ethylene glycol monomethyl ether, ethylene glycol monoethyl ether, propylene glycol monoethyl ether, diethylene glycol monoethyl ether, diethylene glycol monobutyl ether and dipropylene glycol monoethyl ether; monoacetates of a glycol such as ethylene glycol monoacetate and propylene glycol monoacetate; and glycols such as ethylene glycol, diethylene glycol, trimethylene glycol, triethylene glycol, tetraethylene glycol, polyethylene glycol, propylene glycol and butanediol.

Out of these, alcohols and glycols are preferred, and alcohols having 1 to 8 carbon atoms and glycols having 2 to 18 carbon atoms are more preferred. Lower alcohols having 1 to 6 carbon atoms are particularly preferred as they reduce the average particle diameter of the obtained charge control agent, and n-butanol is most preferred.

In the present invention, the azo-based iron complex salt compound of the general formula (2) which is formed by the above ironizing reaction contains a hydrogen ion ($H^+$) and an alkali metal ion (for example, $Na^+$ or $K^+$) derived from the basic compound which is used to control pH as cations $A^+$. That is, generally, the azo-based iron complex salt compound is formed in a mixed state of a hydrogen atom ($H^+$) and an alkali metal ion as cations $A^+$.

Therefore, the reaction product containing the azo-based iron complex salt compound may be extracted directly in the present invention but it is preferred to subject this reaction product to an alkali treatment. This alkali treatment increases the content of the alkali metal ion contained as a cation $A^+$ and also can change all the cations $A^+$ to alkali metal ions.

This alkali treatment may be carried out by cooling or leaving the reaction solution to be cooled (generally to about 50° C. or lower, preferably to 40° C. or lower) after the end of the ironizing reaction and then adding an aqueous solution of an alkali metal hydroxide dropwise to the reaction solution. The alkali metal hydroxide used herein is preferably sodium hydroxide from the viewpoints of the object of the present invention, material cost and handling ease. It is recommended to add the alkali metal hydroxide so as to adjust pH to 12.5 or more, preferably 13.5±0.5. When pH is too high, the average particle diameter of the formed azo-based iron complex salt tends to become large.

The reaction solution containing the azo-based iron complex salt obtained as described above may be supplied to the ion exchange step (C) or a post-step which will be described hereinafter directly or after it is filtered and the filtrate is rinsed to obtain a wet cake containing the azo-based iron complex salt or a dried product thereof.

(C) Ion Exchange Step:

In this ion exchange step (C), cationic species other than the alkali metal ion, for example, an ammonium ion is introduced through ion exchange, and the introduction of the ammonium ion can further improve charging ability.

The ammonium ion is represented by the following formula (3):

$$(X)_4 \cdot N^+ \tag{3}$$

In the above formula, X is a hydrogen atom or an organic group, and a plurality of X's may be the same or different and may be bonded together to form a ring.

Typical examples of the above organic group are an alkyl group and an alkenyl group all of which may have a halogen atom, hydroxyl group, alkoxy group, amino group, alkyl-substituted amino group, aryl group (such as phenyl group or naphthyl group) or heterocyclic group as a substituent.

The ion exchange step for introducing the ammonium ion is carried out by using an ammoniumizing agent containing the above ammonium ion, for example, a solution of an inorganic ammonium salt such as ammonium nitrate, ammonium phosphate, ammonium chloride, ammonium sulfate or ammonium phosphate. Although it is preferred to use the aqueous solution of an inorganic ammonium salt (particularly ammonium chloride or ammonium sulfate) as the ammoniumizing agent, for example, a solution of an acid salt of an organic amine (for example, hydrogen chloride salt) represented by the following formula (4):

$$(X)_3 \cdot N^+ \tag{4}$$

(In the above formula, X is as defined in the above formula (3) and at least one of X's is an organic group)

or a solution of a quaternary ammonium salt derived from the acidic salt of an organic amine (solution containing water or a mixed solution of water and an organic solvent as a solvent)

may also be used as the ammoniumizing agent. Examples of the above organic amine and the quaternary ammonium salt are given in the above Patent Document 2. Ammonia water may also be used as the ammoniumizing agent.

Further, the above ammoniumizing agents may be used in combination of two or more.

An ion exchange reaction using the above ammoniumizing agent is carried out in an aqueous or non-aqueous system by dissolving or dispersing the reaction solution containing the above azo-based iron complex salt, the wet cake or the dried product in a solvent, adding a solution of this ammoniumizing agent dropwise to this solution and mixing it with the solution, thereby introducing the ammonium ion as the cation $A^+$ through ion exchange with $H^+$ and the alkali metal ion contained in the above azo-based iron complex salt.

It is desired that this ion exchange reaction should be carried out in an aqueous system in which water is used as the solvent from the viewpoints of the easy crystallization of the reaction product and cost.

It is preferred that pH of the reaction solution after the ammoniumizing agent is added dropwise should be kept at 7.8±1.0 because the ammonium ion is ion exchanged efficiently.

Further, the reaction temperature is preferably 80° C. or higher, more preferably 90° C. or higher. The reaction time is about 5 to 8 hours.

The amount of the ammoniumizing agent may be determined according to the amount of the ammonium ion to be introduced. The ammoniumizing agent is desirably used in an amount of generally 86 mol % or more, particularly preferably 90 mol % or more in terms of the ammonium ion based on the total of cations $A^+$.

In the above-described ion exchange step, an acid such as hydrochloric acid, nitric acid or sulfuric acid may be used as an ion exchange agent, thereby making it possible to increase the amount of $H^+$ as a cation $A^+$.

Further, a cation such as $Na^+$ can be introduced through ion exchange using the above-described aqueous solution of an alkali metal hydroxide as the ion exchange agent without carrying out the above-described alkali treatment.

As a matter of course, the ion exchange agent may be used in combination with the above-described ammoniumizing agent. Even when this ion exchange agent is used, it is desired to keep pH at 7.8±1.0.

(D) Post-Step:

The charge control agent containing an azo-based iron complex salt represented by the general formula (2) can be obtained as described above. In the present invention, the yield of the azo-based iron complex salt is high, a side-reaction is rare, the purity of the azo-based iron complex salt is high, the primary particle diameter of the crystal of the formed azo-based iron complex salt is small, and this azo-based iron complex salt can be used as a charge control agent directly by carrying out post-treatments which are generally carried out, such as filtration, rinsing, drying and pulverization. That is, a special purification treatment is not necessary, thereby making it possible to greatly cut the production cost.

For example, the reaction solution containing an azo-based iron complex salt compound represented by the general formula (2) obtained through the above-described iron complex salt forming step (or an alkali treatment after that) and the ion exchange step is filtered by using a filter such as a Nutsche filter to obtain a wet cake by using separation means such as a filter press or a centrifugal filter, and the wet cake is fully washed with water and/or an organic solvent, preferably water, and then dried with a hot air drier or a reduced-pressure drier and optionally pulverized to produce powders composed of fine particles having an average particle diameter of 4 μm or less, particularly 1 to 4 μm as a charge control agent.

That is, since the reaction is carried out while pH is kept at a predetermined range in the above-described iron complex salt forming step (B) in the present invention, the reaction time is shortened, the primary particle diameter of the crystal of the obtained iron complex salt compound is extremely small, and therefore an agglomerate thereof has a small particle diameter and is fragile. As a result, the iron complex salt compound can be disintegrated into fine particles which are suitably dispersed in a binder uniformly, for example, primary particles having an average particle diameter of 4 μm or less, or fine particles close in size to primary particles without pulverizing it, thereby making it possible to obtain a high-quality charge control agent which is uniform in shape and stable in charging characteristics. Even when the compound is pulverized, fine particles having an average particle diameter of 4 μm or less can be easily obtained by pulverization with weak force using a stirring mill or a mortar.

For example, when pH control is not carried out in the iron complex salt forming step (B), the primary particle diameter of the crystal of the formed iron complex salt compound is large with the result that an agglomerate thereof has a large particle diameter and hardly collapses, and the above fine particles cannot be obtained without using special grinding means such as grinding in a high-speed gas stream such as a jet mill or ultrasonic grinding.

Thus, fine particles can be obtained without carrying out pulverization or by pulverization with weak force, thereby making it possible to cut cost as well.

<Charge Control Agent>

The charge control agent obtained as described above contains an azo-based iron complex salt represented by the general formula (2) as the main component in an amount of, for example, 90 wt % or more, particularly 95 wt % or more and is used for various purposes as a negative charge control agent for charging negatively by friction.

In the charge control agent produced as described above, compounds represented by the following formulas (2a) to (2g) are preferred as the iron complex salt compound of the general formula (2) to be formed in the above-described iron complex salt forming step (B).

(2a)

(2b)

(2c)

(2d)

(2e)

(2f)

(2g)

Out of the above compounds of the above formulas (2a) to (2g), a compound containing an ammonium ion ($NH_4^+$) in an amount of 86 mol % or more, particularly 90 mol % or more based on the total of all the cations $A^+$ is most preferred.

Since the charge control agent obtained by the production process of the present invention has a very small particle diameter, it has high dispersibility in resins and is advantageously used as a negative charge control agent which is mixed with a toner used to develop an electrostatic image in the electrophotographic field and a powder coating material used in the electrostatic coating field.

The above charge control agent can be mixed with a toner by totally the same means as a conventionally known charge control agent, and the amount thereof may be the same as that of the conventionally known charge control agent.

Taking a toner as an example, a toner for development having predetermined negatively charging characteristics is obtained by melt kneading this charge control agent with a toner binder resin known per se together with other toner additives (such as a colorant, a wax and magnetic powders), grinding the kneaded product to a suitable particle size and classifying the obtained particles.

A toner for development comprising this charge control agent can also be obtained by mixing the above charge control agent into a monomer forming a binder resin together with predetermined toner additives and carrying out the emulsion polymerization or suspension polymerization of the obtained monomer composition to form a binder resin.

Further, this charge control agent can be fixed onto the surfaces of toner particles mechanochemically by dry mixing powders of the charge control agent obtained by the above process with the toner particles which are formed in advance together with a flowability improving agent such as fine powder silica.

As a matter of course, the charge control agent obtained by the above-described process can be mixed with a toner together with another charge control agent which is produced by a process known per se.

A toner for development comprising the charge control agent (non-magnetic toner) may be mixed with a known magnetic carrier (or a resin coated magnetic carrier) or carrier particles such as glass beads to be used as a two-component developer. A toner comprising magnetic powders and the charge control agent is used as a one-component developer to form an image by electrophotography.

A toner for developing an electrostatic image comprising the charge control agent obtained by the above process (negatively chargeable toner) has quick charging risetime, can provide a sufficiently large amount of charge and can maintain a stable amount of charge.

Since the particle diameter of the charge control agent is very small, the charge control agent can friction charge negatively and homogeneously and can form a uniform, clear high-quality image. Since this toner for development in particular has quick charging risetime, it can form a clear electrostatic latent image at the time of not only high-speed copying but also low-speed copying at a maximum circumferential speed of a photosensitive drum of 600 cm/min or less. Thus, a clear high-resolution image can be formed without a fog.

Further, a powder coating material comprising the charge control agent produced by the present invention is excellent in environmental resistance, storage stability, particularly heat stability and durability, has an electrostatic coating adhesion efficiency of 100%- and can form a thick film having no coating defect.

EXAMPLES

The following examples are provided for the purpose of further illustrating the present invention but are in no way to be taken as limiting.

In the following examples, "parts" means "parts by mass".

Example 1

Coupling Step 11.9 g of 2-amino-4-chlorophenol, 15.0 ml of concentrated hydrochloric acid and 103 ml of water were added to a reactor, 17.6 g of a 33% (w/v) sodium nitrite aqueous solution was added to the reactor while it was cooled to 5 to 10° C., and these materials were stirred for 2 hours to carry out a diazotization reaction. Then, 0.2 g of sulfamic acid was added to obtain a diazonium salt solution.

Then, 22.1 g of Naphthol AS, 22.86 g of a 25% (w/v) sodium hydroxide aqueous solution, 73 ml of n-butanol and 183 ml of water were mixed together to prepare a solution, and the diazonium salt solution obtained above was added dropwise to this solution and stirred at 20 to 24° C. for 4 hours while it was confirmed that pH of the solution was in the range of 11 to 12 so as to obtain a solution containing a monoazo compound.

Iron Complex Salt Forming Step:

3.99 g of ammonium chloride, 2.0 g of salicylic acid, 17.3 g of a 38% (w/v) ferric chloride (ironizing agent) aqueous solution and 17.8 g of a 25% (w/v) sodium hydroxide aqueous solution were added to the solution containing a monoazo compound obtained above, and the resulting mixture was heated at 60±5° C. and stirred for 7 hours. During this time, pH of the solution was kept at 7.0 to 7.5 by using the 25 (w/v) sodium hydroxide aqueous solution.

17.0 g of a 25% (w/v) sodium hydroxide aqueous solution was added to the obtained solution containing an azo-based iron complex salt, and the resulting mixture was heated at 40° C. or higher and stirred for 2 hours to carry out an alkali treatment. During this time, pH of the solution was kept at 13.4 or more by using the 25% (w/v) sodium hydroxide aqueous solution.

The precipitated azo-based iron complex salt was obtained as a wet cake by filtration with a Nutsche filter, and the wet cake was washed with 300 ml of water.

Ion Exchange Step:

The wet cake obtained above was put into a reactor, 300 ml of water and 3.8 g of ammonium sulfate were added to the reactor, and these materials were heated at 80° C. and stirred for 6 hours to carry out ion exchange. During this time, it was confirmed that pH was in the range of 7.8±0.5.

Post-Step:

The obtained reaction solution was cooled to room temperature, the precipitated azo-based iron complex salt was obtained as a wet cake by filtration with a Nutsche filter, and the wet cake was washed with 350 ml of water.

When the obtained wet cake was transferred to a hot air drier to be dried at 110° C. for one day, charge control agent powders having an average particle diameter of 1 to 2 μm were obtained.

This charge control agent comprised an azo-based iron complex salt represented by the following structural formula (2') as an effective component.

(2')

The above azo-based iron complex salt contained a hydrogen ion, a sodium ion and an ammonium ion as cations ($A^+$).

When the purity and yield (%) of this azo-based iron complex salt were analyzed by high-speed liquid chromatography (to be abbreviated as HPLC hereinafter), they were 99.0% or more and 95.6%, respectively.

The measurement conditions of HPLC were as follows.
Pump: L-2130 of Hitachi High-Technologies Corporation
Detector: L-2455 of Hitachi High-Technologies Corporation
Column: YMC-Pack Pro C18RS of YMC Co., Ltd. (5 μm, inner diameter of 4.6 mm, column length of 250 mm)
Column temperature: 40° C.
Mobile phase: acetonitrile/37.5 mM sodium acetate water=85/15 (v/v)
Flow rate: 1.0 ml/min
Sample concentration: 200 mg/L The time required from the coupling step to the time when the final dried product was taken out was about one week.

The following physical and chemical analysis and evaluation of physical properties were made on the obtained charge control agent.

(Observation Through Scanning Electron Microscope)

Figure 1:
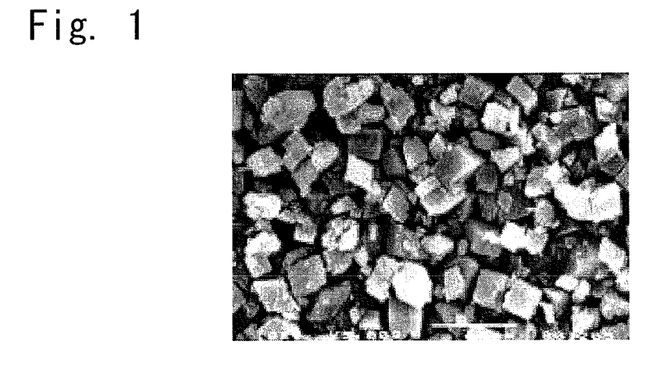
FIG. 1 This is a scanning electron photomicrograph of a charge control agent obtained in Example 1.

A scanning electron microscope (JSM-220T (of JEOL LTD.)) was used to observe the particle diameter and shape of a sample. When the sample was magnified for observation, the particle diameter of the primary particle was 1 to 4 μm. An electron photomicrograph of this particle (primary particle) is shown in FIG. 1.

(Measurement of Average Particle Diameter of Charge Control Agent)

About 20 mg of the charge control agent was added to a solution containing 0.2 ml of Dry Well (trade name of Fuji Photo Film Co., Ltd.) and 30 ml of water to prepare a mixed solution, and about 1 ml of this mixed solution was added to about 300 ml of dispersed water in a particle size distribution meter (PRO7000S SK Laser Microsizer of Seishin Enterprise Co., Ltd.) to apply ultrasonic vibration to the resulting solution for 3 minutes so as to measure the particle size distribution.

The average particle diameter of the charge control agent was 1.64 μm.

It was understood from this that agglomerated particles were obtained in the form of fine particles disintegrated to the level of primary particles without carrying out pulverization.

(Specific Surface Area of Charge Control Agent)

A specific surface area meter (FlowSorb II 2300 of Shimadzu Corporation) was used to measure the specific surface area (BET) of the charge control agent. An empty cell (9 mm in size) was weighed, and the sample was filled into the cell up to about ⅘ (about 0.2 g) of its capacity. The cell was set in a drying chamber and heated at 60° C. for 30 minutes to be deaerated. After the cell was left to be cooled, it was weighed to calculate the weight of the sample so as to measure the specific surface area of the sample. As a result, the specific surface area of the charge control agent (primary particle crystal) calculated from the average particle diameter was 8.05 $m^2/g$.

Comparative Example 1

Coupling Step

A diazonium salt solution was obtained in the same manner as in Example 1.

Then, 22.1 g of Naphthol AS, 11.0 ml of a 25% (w/v) sodium hydroxide aqueous solution, 38.9 g of a 15% (w/v) sodium carbonate aqueous solution, 153 ml of n-butanol and 105 ml of water were mixed together to prepare a solution, and the diazonium salt solution obtained above was added dropwise to this solution and stirred at 21±3° C. for 4 hours while pH was kept at 11.0±0.5 to obtain a solution containing a monoazo compound.

After an organic layer was collected from the obtained monoazo compound solution by carrying out separation operation, 8.0 ml of a 25% (w/v) sodium hydroxide aqueous solution and 110 ml of water were added and stirred for 2 hours. Further, an organic layer was collected by carrying out separation operation.

Iron Complex Salt Forming Step;

17.0 g of a 38% (w/v) ferric chloride aqueous solution and 38.5 g of a 15% (w/v) sodium carbonate aqueous solution were added to the obtained organic layer containing a monoazo compound and stirred for 8 hours while 5.7 g of salicylic acid, 30.0 ml of n-butanol, 50.0 ml of water and 19.0 g of a 15% (w/v) sodium carbonate aqueous solution were added under agitation.

After an organic layer was collected from the obtained solution containing an azo-based iron complex salt by carrying out separation operation, 5.0 ml of a 25% (w/v) sodium hydroxide aqueous solution and 75 ml of water were added and stirred for 2 hours. The precipitated azo-based iron complex salt was obtained as a wet cake by filtration with a Nutsche filter, and the wet cake was washed with 300 ml of water.

Ion Exchange Step:

The obtained wet cake and 140 ml of water were added to a reactor to be dispersed, and 87 ml of water and 3.8 g of ammonium sulfate were further added and heated at 92 to 97° C. for 1 hour under agitation.

Post-Step:

The obtained reaction solution was cooled to room temperature, the precipitated azo-based iron complex salt was obtained as a wet cake by filtration with a Nutsche filter, and the wet cake was washed with 350 ml of water.

The obtained wet cake was transferred to a hot air drier to be dried at 110° C. for one day so as to obtain a charge control agent comprising an iron complex salt compound represented by the above structural formula (2') as an effective component.

The above azo-based iron complex salt contained a hydrogen ion, a sodium ion and an ammonium ion as cations ($A^+$).

When the purity and yield (%) of this azo-based iron complex salt were analyzed by HPLC, they were 99.0% or more and 89%, respectively.

The time required from the coupling step to the time when the final dried product was taken out was about 10 days.

Physical and chemical analysis and the evaluation of physical properties were made on this charge control agent in the same manner as in the above Example 1.

As a result, the average particle diameter of the charge control agent which was agglomerated particles was 6.48 μm, the average particle diameter of primary particle crystals obtained by finely grinding the charge control agent with a jet mill was 1.85 μm, and the specific surface area of the primary particle crystal was 7.53 $m^2/g$.

Figure 2:
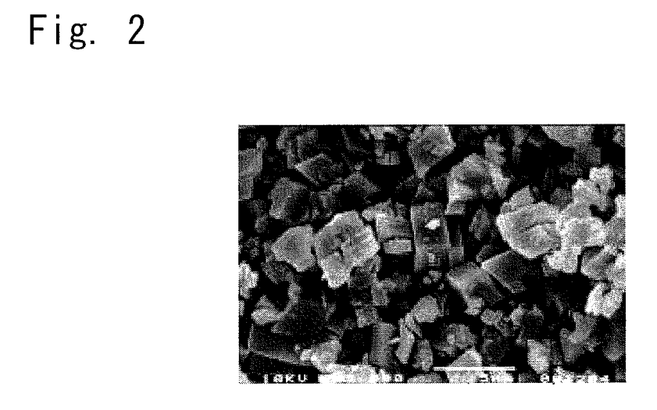
FIG. 2 This is a scanning electron photomicrograph of a charge control agent obtained in Comparative Example 1.

An electron photomicrograph of this charge control agent (primary particle) is shown in FIG. 2.

<Evaluation of Charge Control Agent of Example 1>

(Production of Non-Magnetic Toner)

91 parts of a styrene-acrylate copolymer resin (CPR-100 of Mitsui Chemicals, Inc. having an acid value of 0.1 mgKOH/g), 1 part of the charge control agent produced in Example 1, 5 parts of carbon black (MA-100 of Mitsubishi Chemical Corporation) and 3 parts of low-molecular weight polypropylene (VISCOL 550P of Sanyo Chemical Industries, Ltd.) were melt mixed together by means of a mixer (double-screw extrusion kneader) under heating at 130° C.

This molten mixture was cooled, roughly ground by means of a hammer mill and then finely ground by means of a jet mill, and the obtained particles were classified to obtain a non-magnetic toner having a volume average particle diameter of 9±0.5 μm.

(Evaluation Tests)

4 parts of this toner was mixed with 100 parts of an uncoated ferrite carrier (F-150 of Powdertech Co., Ltd.) and shaken to be charged negatively, and then the amount of charge was measured by mean of a blow-off powder charge quantity meter. As a result, it was −22.0 μc/g.

A time constant (τ) which is an index of charging rise-up property was also calculated. The time constant (τ) was obtained by measuring the amount of charge until saturation charge was reached at predetermined time intervals by means of a blow-off powder charge quantity meter to obtain $\ln(q^{max}-q)$ from the following expression and plotting the relationship between time t and $\ln(q^{max}-q)$ on a graph. As a result, the time constant was 208 s.

$$(q^{max}-q)/(q^{max}-q^0)=\exp(-t/\tau)$$

$q^{max}$ is the amount of saturation charge, $q^0$ is the amount of initial charge (in this case, when the charging time is 10 seconds), t is a measurement time, and q is the amount of charge at that time.

When the charging rise-up property is better, the time constant becomes smaller. The unit of the time constant is second.

When the toner was mixed with a silicon-coated ferrite carrier (F96-150 of Powdertech Co., Ltd.), the amount of charge and the time constant were also evaluated. As a result, the amount of charge was −14.9 μc/g and the time constant was 50 s.

<Evaluation of Charge Control Agent of Comparative Example 1>

For comparison, a nonmagnetic toner was prepared in the same manner as above except that the charge control agent produced in Comparative Example 1 was used in place of the charge control agent produced in Example 1, and the same evaluation tests as above were made on this toner.

As a result, when an uncoated ferrite carrier (F150 of Powdertech Co., Ltd.) was used, the amount of charge was −17.8 μc/g and the time constant was 370 s.

When a silicon-coated ferrite carrier (F96-150 of Powdertech Co., Ltd.) was used, the amount of charge was −12.7 μc/g and the time constant was 143 s.

As obvious from the above results, it was understood that a toner comprising the charge control agent obtained by the production process of the present invention has improved charging rise-up property and a large amount of charge.

<Evaluation of Environmental Stability>

The environmental stability of charge was also evaluated.

The method of evaluating environmental stability was carried out by measuring the amount of charge of a non-magnetic toner prepared in the above evaluation tests under a normal environment (25° C.—50% RH (relative humidity)) and the amount of charge of the toner under a high temperature-high humidity environment (35° C.—85% RH).

As for the measurement of the amount of charge, the amount of saturation charge was measured with a blow-off powder charge quantity meter by fully charging a developer which was exposed to each of the above environments for 24 hours while it was left in that environment. The environmental stability was judged by a variation in the amount of charge between the two exposure environments. The environmental variation was calculated from the following expression.

Environmental variation=100×(A−B)/A

A is the amount of charge under a normal environment, and B is the amount of charge under a high temperature-high humidity environment.

A toner having higher environmental stability has a smaller environmental variation.

A toner was judged as excellent (◉) when its environmental variation was less than 10%, as good (○) when its environmental variation was 10 to 25%, as slightly bad (Δ) when its environmental variation was 25 to 40%, and as unacceptable (X) when its environmental variation was more than 40%. The results are shown in Table 1.

TABLE 1

| | Environmental stability | | | |
|---|---|---|---|---|
| Toner | *1 (μC/g) | *2 (μC/g) | environmental variation (%) | Stability |
| Ex. 1 | −22.0 | −18.0 | 18 | ○ |
| Comp. Ex. 1 | −17.8 | −13.0 | 27 | Δ |

*1: Amount of charge under normal environment
*2: Amount of charge under high temperature-high humidity environment As clear from the results of Table 1, it is understood that toner containing the charge control agent obtained by the production process of the present invention has excellent charging ability and improved environmental stability under a high temperature-high humidity environment.

That is, high charging ability can be provided to toner and environmental stability under a high temperature-high humidity environment can be improved by using the charge control agent obtained by the production process of the present invention.

INDUSTRIAL FEASIBILITY

According to the production process of the present invention, a high-purity azo-based iron complex salt can be produced by carrying out a reaction in the iron complex salt forming step (B) while pH is controlled, thereby making it possible to eliminate a purification step. Therefore, the time required for production can be greatly shortened, and the reaction yield can be greatly improved. Thereby, it is possible to significantly cut the production cost.

The charge control agent obtained by the production process of the present invention apparently has higher charging ability and more excellent environmental stability than those of a conventional charge control agent. Further, it does not contain a heavy metal such as a chromium compound which it is apprehended might cause an environmental problem and can provide an extremely useful toner.

What is claimed is:

1. A process for producing a charge control agent comprising an azo-based iron complex salt compound as an effective component, comprising:

(A) obtaining a monoazo compound represented by the following general formula (1) through diazotization coupling:

(1)

wherein,
  p is an integer of 0 to 4 indicative of the number of $R^1$ group(s),
  q and s are each an integer of 0 to 5 indicative of the numbers of $R^2$ group(s) and $R^3$ group(s), respectively, and
  $R^1$ to $R^3$ are each a deuterium atom, halogen atom, nitro group, hydroxyl group, alkyl group, alkenyl group, alkyloxy group, sulfonalkyl group, alkylsulfonate group, sulfonate group, carboxyl group, carboxyester group, sulfonamide group, acetylamino group, benzoylamino group, aromatic hydrocarbon group or aromatic heterocyclic group, with the proviso that when a plurality of $R^1$ groups, $R^2$ groups or $R^3$ groups are existent, said $R^1$ groups, said $R^2$ groups or said $R^3$ groups may be different from one another; and
(B) ironizing the monoazo compound in a solvent while pH is kept at 7.0 to 8.0 and the temperature is maintained at $60\pm10°$ C., to produce an azo-based iron complex salt compound represented by the following general formula (2):

wherein, p, q, s and $R^1$ to $R^3$ are as defined in the above general formula (1), and $A^+$ is a cation;
wherein said azo-based iron complex has an average particle diameter of not more than 4 μm.

2. The process for producing a charge control agent according to claim 1 which further comprises:
  (C) introducing an ammonium ion as cationic species into the charge control agent through ion exchange.

3. The process of producing a charge control agent according to claim 2, wherein not less than 86 mol % of cations $A^+$ in said azo-based iron complex are ammonium ions.

\* \* \* \* \*